(12) United States Patent
Lutter et al.

(10) Patent No.: US 9,095,433 B2
(45) Date of Patent: Aug. 4, 2015

(54) TRUNCATED CONE HEART VALVE STENT

(76) Inventors: Georg Lutter, Kiel (DE); Lucian Lozonschi, Madison, WI (US)

( * ) Notice: Subject to any disclaimer, the term of this patent is extended or adjusted under 35 U.S.C. 154(b) by 48 days.

(21) Appl. No.: 13/275,683

(22) Filed: Oct. 18, 2011

(65) Prior Publication Data
US 2012/0035713 A1 Feb. 9, 2012

Related U.S. Application Data

(63) Continuation of application No. 12/677,958, filed as application No. PCT/DE2008/001515 on Sep. 10, 2008, now abandoned.

(30) Foreign Application Priority Data

Sep. 13, 2007 (DE) .......................... 10 2007 043 830

(51) Int. Cl.
*A61F 2/24* (2006.01)
*A61B 17/04* (2006.01)
*A61B 17/00* (2006.01)

(52) U.S. Cl.
CPC ........... *A61F 2/2418* (2013.01); *A61B 17/0401* (2013.01); *A61B 2017/00243* (2013.01); *A61B 2017/0496* (2013.01); *A61F 2/2436* (2013.01); *A61F 2/2457* (2013.01); *A61F 2/2487* (2013.01); *A61F 2220/0008* (2013.01); *A61F 2230/005* (2013.01); *A61F 2230/0054* (2013.01); *A61F 2230/0078* (2013.01); *A61F 2250/001* (2013.01)

(58) Field of Classification Search
CPC ........................................................ A61F 2/24
USPC ................................................ 623/2.17, 1.26
See application file for complete search history.

(56) References Cited

U.S. PATENT DOCUMENTS

| | | |
|---|---|---|
| 3,409,013 A | 11/1968 | Berry |
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |

(Continued)

FOREIGN PATENT DOCUMENTS

| | | |
|---|---|---|
| DE | 1001074 | 5/1955 |
| DE | 2246526 | 3/1973 |

(Continued)

OTHER PUBLICATIONS

Ma L., et al., Double-crowned valved stents for off-pump mitral valve replacement. Eur J Cardiothorac Surg. Aug. 2005, 28(2): 194-198.

(Continued)

*Primary Examiner* — Thomas J Sweet
*Assistant Examiner* — Matthew Schall

(57) ABSTRACT

A heart valve stent having a section with a heart valve implant and several proximally disposed tissue anchors, also comprising a plurality of anchoring threats, each with a proximate end fastened to the stent or valve and a distal end attached to tissue within a heart chamber to provide tension between the heart chamber tissue and the stent.

11 Claims, 11 Drawing Sheets

(56) References Cited

U.S. PATENT DOCUMENTS

Figure 1:
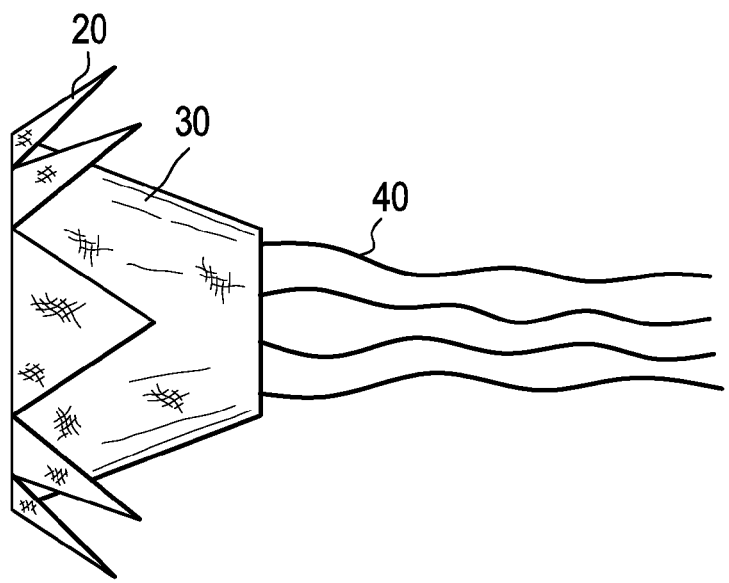

| | | |
|---|---|---|
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Weinhold |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely |
| 5,554,185 A | 9/1996 | Block et al. |
| 5,571,175 A | 11/1996 | Vanney et al. |
| 5,591,185 A | 1/1997 | Kilmer et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,697,905 A | 12/1997 | Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,741,333 A | 4/1998 | Frid |
| 5,749,890 A | 5/1998 | Shaknovich |
| 5,756,476 A | 5/1998 | Epstein |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler |
| 5,855,602 A | 1/1999 | Angell |
| 5,925,063 A | 7/1999 | Khosravi |
| 5,957,949 A | 9/1999 | Leonhardt et al. |
| 5,993,481 A | 11/1999 | Marcade et al. |
| 6,027,525 A | 2/2000 | Suh et al. |
| 6,045,497 A | 4/2000 | Schweich, Jr. et al. |
| 6,077,214 A | 6/2000 | Mortier et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian |
| 6,302,906 B1 | 10/2001 | Goecoechea et al. |
| 6,332,893 B1 | 12/2001 | Mortier et al. |
| 6,350,277 B1 | 2/2002 | Kocur |
| 6,358,277 B1 | 3/2002 | Duran |
| 6,402,679 B1 | 6/2002 | Mortier et al. |
| 6,402,680 B2 | 6/2002 | Mortier et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,482,228 B1 | 11/2002 | Norred |
| 6,488,704 B1 | 12/2002 | Connelly et al. |
| 6,537,198 B1 | 3/2003 | Vidlund et al. |
| 6,569,196 B1 | 5/2003 | Vesely et al. |
| 6,582,462 B1 | 6/2003 | Andersen et al. |
| 6,605,112 B1 | 8/2003 | Moll |
| 6,616,684 B1 | 9/2003 | Vidlund et al. |
| 6,622,730 B2 | 9/2003 | Ekvall et al. |
| 6,629,921 B1 | 10/2003 | Schweich, Jr. et al. |
| 6,652,578 B2 | 11/2003 | Bailey et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,471 B2 | 6/2004 | Mortier et al. |
| 6,764,510 B2 | 7/2004 | Vidlund et al. |
| 6,810,882 B2 | 11/2004 | Langberg et al. |
| 6,830,584 B1 | 12/2004 | Seguin |
| 6,893,460 B2 | 5/2005 | Spenser et al. |
| 6,908,424 B2 | 6/2005 | Mortier et al. |
| 6,908,481 B2 | 6/2005 | Cribier |
| 6,936,067 B2 | 8/2005 | Buchanan |
| 6,955,175 B2 | 10/2005 | Stevens et al. |
| 6,974,476 B2 | 12/2005 | McGuckin et al. |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,077,862 B2 | 7/2006 | Vidlund et al. |
| 7,100,614 B2 | 9/2006 | Stevens et al. |
| 7,101,395 B2 | 9/2006 | Tremulis et al. |
| 7,112,219 B2 | 9/2006 | Vidlund et al. |
| 7,141,064 B2 | 11/2006 | Scott et al. |
| 7,175,656 B2 | 2/2007 | Khairkhahan |
| 7,201,772 B2 | 4/2007 | Schwammenthal et al. |
| 7,247,134 B2 | 7/2007 | Vidlund et al. |

(56) References Cited

U.S. PATENT DOCUMENTS

| | | |
|---|---|---|
| 7,276,078 B2 | 10/2007 | Spenser et al. |
| 7,276,084 B2 | 10/2007 | Yang et al. |
| 7,316,706 B2 | 1/2008 | Bloom et al. |
| 7,329,278 B2 | 2/2008 | Seguin et al. |
| 7,374,571 B2 | 5/2008 | Pease et al. |
| 7,381,218 B2 | 6/2008 | Schreck |
| 7,393,360 B2 | 7/2008 | Spenser et al. |
| 7,404,824 B1 | 7/2008 | Webler |
| 7,416,554 B2 | 8/2008 | Lam et al. |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,556,646 B2 | 7/2009 | Yang et al. |
| 7,585,321 B2 | 9/2009 | Cribier |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,308 B2 | 12/2009 | Loulmet |
| 7,674,222 B2 | 3/2010 | Nikolic et al. |
| 7,748,389 B2 | 7/2010 | Salahieh et al. |
| 7,766,961 B2 | 8/2010 | Patel et al. |
| 7,803,184 B2 | 9/2010 | McGuckin, Jr. et al. |
| 7,803,185 B2 | 9/2010 | Gabbay |
| 7,837,727 B2 | 11/2010 | Goetz et al. |
| 7,892,281 B2 | 2/2011 | Seguin et al. |
| 7,896,915 B2 | 3/2011 | Guyenot et al. |
| 7,927,370 B2 | 4/2011 | Webler et al. |
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 8,043,368 B2 | 10/2011 | Crabtree |
| 8,052,749 B2 | 11/2011 | Salahieh |
| 8,052,750 B2 | 11/2011 | Tuval et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino |
| 8,167,934 B2 | 5/2012 | Styrc et al. |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,252,051 B2 | 8/2012 | Chau et al. |
| 8,303,653 B2 | 11/2012 | Bonhoeffer et al. |
| 2002/0139056 A1 | 10/2002 | Finnell |
| 2003/0010509 A1 | 1/2003 | Hoffman |
| 2003/0078652 A1 | 4/2003 | Sutherland |
| 2004/0064014 A1 | 4/2004 | Melvin et al. |
| 2004/0092858 A1 | 5/2004 | Wilson et al. |
| 2004/0127983 A1 | 7/2004 | Mortier et al. |
| 2004/0152947 A1 | 8/2004 | Schroeder et al. |
| 2004/0163828 A1 | 8/2004 | Silverstein et al. |
| 2005/0004652 A1 | 1/2005 | Van der Burg et al. |
| 2005/0075727 A1 | 4/2005 | Wheatley |
| 2005/0096498 A1 | 5/2005 | Houser et al. |
| 2005/0113810 A1 | 5/2005 | Houser et al. |
| 2005/0113811 A1 | 5/2005 | Houser et al. |
| 2005/0121206 A1 | 6/2005 | Dolan |
| 2005/0125012 A1 | 6/2005 | Houser et al. |
| 2005/0137688 A1 | 6/2005 | Salahieh et al. |
| 2005/0177180 A1 | 8/2005 | Kaganov et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0240200 A1 | 10/2005 | Bergheim |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0161040 A1 | 7/2006 | McCarthy et al. |
| 2006/0161249 A1 | 7/2006 | Realyvasquez et al. |
| 2006/0241745 A1 | 10/2006 | Solem |
| 2006/0259135 A1 | 11/2006 | Navia et al. |
| 2006/0276874 A1 | 12/2006 | Wilson et al. |
| 2007/0016286 A1 | 1/2007 | Herrmann et al. |
| 2007/0050020 A1 | 3/2007 | Spence |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0100439 A1 | 5/2007 | Cangialosi et al. |
| 2007/0112422 A1 | 5/2007 | Dehdashtian |
| 2007/0118151 A1 | 5/2007 | Davidson |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0256843 A1 | 11/2007 | Pahila |
| 2007/0267202 A1 | 11/2007 | Mariller |
| 2008/0071361 A1 | 3/2008 | Tuval et al. |
| 2008/0071362 A1 | 3/2008 | Tuval et al. |
| 2008/0071366 A1 | 3/2008 | Tuval et al. |
| 2008/0071369 A1 | 3/2008 | Tuval et al. |
| 2008/0172035 A1 | 7/2008 | Starksen et al. |
| 2008/0208328 A1 | 8/2008 | Antocci et al. |
| 2008/0243245 A1 | 10/2008 | Thambar et al. |
| 2008/0255661 A1 | 10/2008 | Straubinger et al. |
| 2008/0281411 A1 | 11/2008 | Berreklouw |
| 2009/0076598 A1 | 3/2009 | Salahieh et al. |
| 2009/0082619 A1 | 3/2009 | De Marchena |
| 2009/0099410 A1 | 4/2009 | De Marchena |
| 2009/0112309 A1 | 4/2009 | Jaramillo |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0171432 A1 | 7/2009 | Von Segesser et al. |
| 2009/0171447 A1 | 7/2009 | Von Segesser et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0234318 A1 | 9/2009 | Loulmet et al. |
| 2009/0240320 A1 | 9/2009 | Tuval et al. |
| 2009/0248149 A1 | 10/2009 | Gabbay |
| 2009/0276040 A1 | 11/2009 | Rowe |
| 2009/0319037 A1 | 12/2009 | Rowe et al. |
| 2009/0326575 A1 | 12/2009 | Galdonik et al. |
| 2010/0016958 A1 | 1/2010 | St. Goar et al. |
| 2010/0021382 A1 | 1/2010 | Dorshow et al. |
| 2010/0192402 A1 | 8/2010 | Yamaguchi et al. |
| 2010/0217382 A1 | 8/2010 | Chau |
| 2011/0112632 A1 | 5/2011 | Chau |
| 2011/0137397 A1 | 6/2011 | Chau et al. |
| 2011/0137408 A1 | 6/2011 | Bergheim |
| 2012/0010694 A1 | 1/2012 | Lutter et al. |
| 2012/0035722 A1 | 2/2012 | Tuval |
| 2012/0101571 A1 | 4/2012 | Thambar et al. |
| 2012/0101572 A1 | 4/2012 | Kovalsky et al. |
| 2012/0215303 A1 | 8/2012 | Quadri et al. |

FOREIGN PATENT DOCUMENTS

| | | |
|---|---|---|
| DE | 19532846 | 3/1997 |
| DE | 19546692 | 6/1997 |
| DE | 19857887 | 7/2000 |
| DE | 19907646 | 8/2000 |
| DE | 10010074 A1 | 10/2001 |
| DE | 10049812 | 4/2002 |
| DE | 10049813 | 4/2002 |
| DE | 10049814 | 4/2002 |
| DE | 10049815 | 4/2002 |
| DE | 102006052564 B4 | 12/2007 |
| EP | 0103546 | 3/1984 |
| EP | 0144167 | 6/1985 |
| EP | 0597967 | 12/1994 |
| EP | 0592410 | 10/1995 |
| EP | 0850607 | 7/1998 |
| EP | 1057460 | 12/2000 |
| EP | 1088529 | 4/2001 |
| EP | 1 264 582 A2 | 12/2002 |

(56) References Cited

FOREIGN PATENT DOCUMENTS

| | | |
|---|---|---|
| EP | 1469797 B1 | 10/2004 |
| EP | 1570809 | 9/2005 |
| EP | 1653888 | 5/2006 |
| EP | 2 055 266 A2 | 5/2009 |
| EP | 2 055 266 B1 | 5/2009 |
| FR | 2815844 | 5/2002 |
| FR | 2788217 | 7/2007 |
| GB | 2056023 | 3/1981 |
| NL | 1 017 275 | 8/2002 |
| SU | 1271508 | 11/1986 |
| WO | WO91/17720 | 11/1991 |
| WO | WO92/17118 | 10/1992 |
| WO | WO93/01768 | 2/1993 |
| WO | WO97/24080 | 7/1997 |
| WO | WO98/29057 | 7/1998 |
| WO | WO99/33414 | 7/1999 |
| WO | WO99/40964 | 8/1999 |
| WO | WO99/47075 | 9/1999 |
| WO | WO00/18333 | 4/2000 |
| WO | WO00/41652 | 7/2000 |
| WO | WO 00/44313 | 8/2000 |
| WO | WO00/47139 | 8/2000 |
| WO | WO01/35878 | 5/2001 |
| WO | WO01/49213 | 7/2001 |
| WO | WO01/54624 | 8/2001 |
| WO | WO01/54625 | 8/2001 |
| WO | WO 01/56512 | 8/2001 |
| WO | WO 01/61289 A1 | 8/2001 |
| WO | WO01/62189 | 8/2001 |
| WO | WO01/64137 | 9/2001 |
| WO | WO01/76510 | 10/2001 |
| WO | WO02/22054 | 3/2002 |
| WO | WO02/36048 | 5/2002 |
| WO | WO02/41789 | 5/2002 |
| WO | WO02/43620 | 6/2002 |
| WO | WO02/47575 | 6/2002 |
| WO | WO02/49540 | 6/2002 |
| WO | WO 02/076348 A1 | 10/2002 |
| WO | WO03/003943 | 1/2003 |
| WO | WO03/003949 | 1/2003 |
| WO | WO03/037227 | 5/2003 |
| WO | WO03/047468 | 6/2003 |
| WO | WO/2004/019825 | 3/2004 |
| WO | WO2005/087140 | 9/2005 |
| WO | WO2006/014233 | 2/2006 |
| WO | WO2006/034008 | 3/2006 |
| WO | WO2006/135536 A2 | 12/2006 |
| WO | WO2008/005405 | 1/2008 |
| WO | WO2008/009940 | 1/2008 |
| WO | WO2008/035337 | 3/2008 |
| WO | WO2008125906 | 10/2008 |
| WO | WO2008/147964 | 12/2008 |
| WO | WO2008/150529 | 12/2008 |
| WO | WO2009/024859 | 2/2009 |
| WO | WO2009-026272 | 2/2009 |
| WO | WO2009/033469 | 3/2009 |
| WO | WO/2011/163275 A2 | 12/2011 |

OTHER PUBLICATIONS

Doudjemline Y., et al., Steps toward the percutaneous replacement of atrioventricular valves an experiemental study. J. Am. Coll. Cardiol. Jul. 19, 2005; 46(2): 360-365.

International Search Report from International Application No. PCT/US2009/041754 dated Sep. 25, 2009.

U.S. Appl. No. 13/350,310, filed Jan. 13, 2012, Rowe.

U.S. Appl. No. 13/356,136, filed Jan. 23, 2012, Chau.

C. Orton, "Mitralseal: Hybrid Transcatheter Mitral Valve Replacement," www.acvs.org/symposium/proceedings2011/data/papers/102.pdf, pp. 311, 312.

Liang Ma, et al., "Double-Crowned Valve Stents for Off-Pump Mitral Valve Replacement," European Journal of Cardio-Thoracic Surgery, 2005, vol. 28, pp. 194-199.

Lutter, Georg, et al., "Mitral Valved Stent Implantation," European Journal of Cardio-Thoracic Surgery, 2010, vol. 38, pp. 350-355.

Lozonschi, Lucian, "Transapical Mitral Valved Stent Implantation: A Survival Series in Swine," The Journal of Thoracic and Cardiovascular Surgery, Aug. 2010, vol. 140, Issue 2, pp. 422-426.

M. Tofeig, et al., "Transcatheter Closure of Mid-Muscular Ventricular Septal Defect with an Amplatzer VSD Occluder Device," Heart, vol. 81, 1999, pp. 438-440.

Ma L., et al., "Double-Crowned Valved Stents for Off-Pump Mitral Valve Replacement," Eur J Cardiothorac Surg. Aug. 2005, vol. 28, No. 2, pp. 194-198.

Boudjemline Y., et al., "Steps Toward the Percutaneous Replacement of Atrioventricular Valves an Experimental Study," J. A. Coll. Cardiol. Jul. 19, 2005, vol. 46, No. 2, pp. 360-365.

Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.

Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Serruys, P.W., et al., "Stenting of Coronary Arteries. Are we the Sorcerer's Apprentice?" European Heart Journal (1989) 10, 774-782, pp. 37-45, Jun. 13, 1989.

Kolata, Gina, "Device That Opens Clogged Arteries Gets a Failing Grade in a New Study," nytimes.com, httol/www.nytimes.com/1991/01/03/healthidevice-that-opens-clogged-arteries-oets-a-faili . . . , Jul. 29, 2009, 2 pages.

Urban, M.D., Philip, "Coronary Artery Stenting," Editions Modecine et Hygiene, Geneve, 1991, pp. 5-47.

Al-Khaja, N., et al., "Eleven Years' Experience with Carpentier-Edwards Biological Valves in Relation to Survival and Complications," European Journal of Cardiothoracic Surgery, vol. 3, pp. 305-311, Jun. 30, 2009.

Wheatley, M.D., David J., "Valve Prostheses," Rob & Smith's Operative Surgery, Fourth Edition, pp. 415-424, ButtenNorths 1986.

Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977, vol. 273, No. 1, pp. 55-62.

Watt, A.H., et al. "Intravenous Adenosine in the Treatment of Supraventricular Tachycardia; a Dose-Ranging Study and Interaction with Dipyridamole," British Journal of Clinical Pharmacology (1986), 21, pp. 227-230.

Uchida, Barry T., et al., "Modifications of Gianturco Expandable Wire Stents," AJR:150, May 1988, Dec. 3, 1987, pp. 1185-1187.

Selby, M.D., J. Bayne, "Experience with New Retrieval Forceps for Foreign Body Removal in the Vascular, Urinary, and Biliary Systems," Radiology 1990; 176:535-538.

Inoune, M.D., Kanji, et al., "Clinical Application of Transvenous Mitral Commissurotomy by a New Balloon Catheter," The Journal of Thoracic and Cardiovascular Surgery, vol. 87, pp. 394-402, 1984.

Al Zaibag, Muayed, et al., "Percutaneous Balloon Valvotomy in Tricuspid Stenos's," British Heart Journal, Jan. 1987, vol. 57, No. 1, pp. 51-53.

Lawrence, Jr., M.D., David D., "Percutaneous Endovascular Graft: Experimental Evaluation," Radiology 1897, 163, pp. 357-360.

Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.

Sigwart, Ulrich, "An Overview of Intravascular Stents: Old and New," Chapter 48, Textbook of Interventional Cardiology, 2nd Edition, W. B. Saunders Company, Philadelphia, PA, © 1994, 1990, pp. 803-815.

Rashkind, M.D., William J., "Historical Aspects of Interventional Cardiology: Past, Present, Future," Texas Heart Institute Journal, Interventional Cardiology, pp. 363-367.

(56) References Cited

OTHER PUBLICATIONS

Rosch, M.D., Josef, "The Birth, Early Years and Future of Interventional Radiology," *J Vasc Interv Radio*, 2003, 14, pp. 841-853.

Pavcnik, M.D., Ph.D., Dusan, et al. "Development and Initial Experimental Evaluation of a Prosthetic Aortic Valve for Transcatheter Placement," *Cardiovascular Radiology* 1992; 183:151-154.

Ross, F.R.C.S., DA., "Aortic Valve Surgery," *Guy's Hospital*, London, pp. 192-197, approximately 1968.

Rashkind, M.D., William J., "Creation of an Atrial Septa Defect Withoput Thoracotomy," *Journal of the American Medical Association*, vol. 196, No. 11, Jun. 13, 1966, pp. 173-174.

Porstmann, W., et al., "Der VerschluB des Ductus Arteriosus Persistens ohne Thorakotomie," *Thoraxchirurgie Vaskulare Chirurgie*, Band 15, Heft 2, Stuttgart, im Apr. 1967, pp. 199-203.

Curriculum Vitae of Robert A. Ersek, M.D., FACS, Jul. 10, 2009, http://1Atomi.ersek.com/rae-cv.htm.

International Search Report from corresponding PCT case No. PCT/US2010/058860, dated Aug. 25, 2011.

Buckberg, Gerald, et al., "Restoring Papillary Muscle Dimensions During Restoration in Dilated Hearts," *Interactive Cardiovascular and Thoracic Surgery*, 2005, vol. 4, pp. 475-477.

International Search Report and Written Opinion from corresponding International Patent Application PCT/US2012/050579, dated Feb. 26, 2013.

H. R. Andersen et al., "Transluminal Implantation of Artificial Heart Valves: Description of a New Expandable Aortic Valve and Initial Results with Implantation by Catheter Technique in Closed Chest Pigs," *European Heart Journal*, 1992, Issue 5, vol. 13, pp. 704-708.

Henning Rud Andersen, "Transluminal Catheter Implanted Prosthetic Heart Valves," *International Journal of Angiology*, 1998, Issue 2, vol. 7, pp. 102-106.

L. L. Knudsen et al., "Catheter-Implanted Prosthetic Heart Valves. Transluminal Catheter Implantation of a New Expandable Artificial Heart Valve in the Descending Thoracic Aorta in Isolated Vessels and Closed Chest Pigs," *International Journal of Artificial Organs*, 1993, Issue 5, vol. 16, pp. 253-262.

Nader Moazami et al., "Transliminal Aortic Valve Placement: A Feasibility Study With a Newly Designed Collapsible Aortic Valve," *ASAIO Journal*, Sep./Oct. 1996, Issue 5, vol. 42, pp. M381-M385.

Robert C. Ashton Jr., "Development of an Intraluminal Device for the Treatment of Aortic Regurgitation: Prototype and in Vitro Testing System," *Journal of Thoracic and Cardiovascular Surgery*, 1996, Issue/vol. 112, pp. 979-983.

A. P. Yoganathan et al., "The Current Status of Prosthetic Heart Valves, Polymetric Materials and Artificial Organs," *American Chemical Society*, Mar. 20, 1983, pp. 111-150.

Ellis Greenhalgh et al., "Design and Characterization of a Biometric Prosthetic Aortic Heart Valve," *North Carolina State University*. 1994, p. 137.

Gary Chamberlain, "Ceramics Replace Body Parts," *Design News*, Jun. 9, 1997, Issue 11, vol. 52.

M. Tofeig, et al., "Transcatheter Closure of a Mid-Muscular Ventricular Septal Defect with an Amplatzer VSD Occluder Device," *Heart*, vol. 81, 1999, pp. 438-440.

E. P. M. Roussea et al., "A Mechanical Analysis of the Closed Hancock Heart Valve Prosthesis," *Journal of Biomechanics*, 1998, Issue 7, vol. 21, pp. 545-562.

C. Orton, "Mitralseal: Hybrid Transcatheter Mitral Valve Replacement," Respiratory and Thoracic Surgery, *Symposium: Small Animal Proceedings*, 2011, pp. 311-312.

G. M. Bernacca, et al., "Polyurethane Heart Valves: Fatigue Failure, Calcification, and Polyurethane Structure," Journal of Biomedical Materials Research, Mar. 5, 1997, Issue 3, vol. 34, pp. 371-379.

Kevin Drawbaugh, "Feature—Heart Surgeons Explore Minimally Invasive Methods," Reuters, Jul. 16, 1996.

Shape Memory Alloys, ttp://webdocs.cs.ualberta.ca/~database; Nov. 14, 2012, pp. 1-3.

Gray, *Gray's Anatomy of the Body*, 1974, pp. ?(1-7), 474-479, 497-498.

Reul, et al., "The Geometry of the Aortic Root in Health, at Valve Disease and After Valve Replacement," *Biomechanics*, vol. 23, No. 2, 1990, pp. 181-191.

Choo, et al., "Aortic Root Geometry: Pattern of Differences Between Leaflets and Sinuses of Valsava," *ICR Publisher*, 1999.

Jin, et al., "Aortic Root Geometry and Stentless Porcine Valve Competence," *Seminars in Thoracic and Cardiovascular Surger*, vol. 11, No. 4, Suppl. 1, Oct. 1999, pp. 145-150.

Webb, et al., "Percutaneous Aortic Valve Implantation Retrograde from the Femoral Artery," *American Heart Association, Inc.*, 2006; pp. 841-850.

Declaration of Malcolm J. R. Dalrymple-Hay, Nov. 9, 2012, pp. 1-11; with Curriculum Vitae, Oct. 4, 2012.

TRUNCATED CONE HEART VALVE STENT

CROSS REFERENCE TO RELATED APPLICATIONS

This application is a continuation of U.S. patent application Ser. No. 12/677,958, filed Sep. 9, 2010, (now abandoned), which claims priority under 35 U.S.C. §371 to, and is a U.S. national phase entry of, PCT/DE2008/001515, filed Sep. 10, 2008, which claims priority to German application no. 10 2007 043 830.5, filed Sep. 13, 2007, each of which is incorporated herein by reference in its entirety.

STATEMENT REGARDING FEDERALLY SPONSORED RESEARCH OR DEVELOPMENT

No federal government funds were used in researching or developing this invention.

BACKGROUND

Field of Invention

The invention refers to a valve stent with a section equipped to receive a heart valve implant and several of proximally disposed anchoring elements.

Such heart valve stents are known in various forms for the replacement dysplastic and degenerated heart valves. Thereby, the surgical implantation of heart valve prostheses is regularly accomplished in the cardioplegic heart. The old, functionally degenerated heart valve is resected and the new, implantable heart valve is sewed in.

However, when the mitral valve is affected, one tries, as far as possible, to maintain the old valve in spite of its malfunctioning so that the entire dynamic mitral valve apparatus is not disturbed. The reason for this is that, for instance, the chordae tendineae, which are attached to the mitral valve are very important for ventricular function. Therefore, they should preferably not be removed from the old mitral valve.

Ideally, the mitral valve (in case the old valve cannot be reconstructed) will be pushed aside as far as possible to make room for a new valve. Space does not play such an important role as compared to the aortic annulus which can be more easily stenosed (i.e., during displacement of the old aortic valve for sole percutaneous implantation).

The chordae tendineae of the mitral valve shall be, if possible, structurally maintained to preserve the ventricular geometry and hence of the left ventricle or achieve optimal function of the left chamber as far as possible. Therefore, a best possible function of the left chamber is obtained and achieved. Of significant relevance is that the anterior mitral valve leaflet is not pushed aside into the free space toward the left ventricle, but rather that it is attached to the mitral annulus so that a press forward of the anterior leaflet into the left ventricular outflow tract (LVOT) is avoided ("sam" phenomenon: systolic anterior movement). This is extremely important, because otherwise a left heart decompensation (massive dysfunction of the left ventricle) could rapidly occur.

Surgically the old mitral valve is attached to the old annulus so that there is a free flow of blood through the valve and both adjacent heart chambers. After pushing aside (attachment of the valve onto the annulus) the heart valve prosthesis is surgically implanted into the annulus.

This extensive method mandatorily takes place with the help of a heart- and lung-machine. For high risk patients it is usually not used and minimally invasive and percutaneous methods to perform the implantation of a heart valve are sought.

In this context, the German patent DE 195 46 692 C2 and the corresponding EP 1 469 797 B1 is known. This patent describes a self-expanding heart valve prosthesis for the implantation into a human body using a catheter system with a heart valve and a foldable, valve-connected and expanding stent. Such a self-expanding heart valve prosthesis can be directed through the femoral artery with the help of a catheter based system to the area of cardiac implantation. After the stent reaches the area of implantation, it can be successively unfolded. Along its long axis, the stent is composed of several, at angles to each other, self-expanding segments that are unfolded gradually. After expansion, the heart valve prosthesis can be anchored with the support of hooks at least in the respective blood vessel close to the heart.

Another apparatus for the fixation and anchorage of heart valve prostheses is described in the German Patent 100 10 074 A1 which fundamentally consists of wire-like elements attached together. Different brackets are hereby used to secure anchorage and brace a heart valve.

Even with the known solutions there is still the danger that a heart valve will be incorrectly implanted due to wrong positioning and deficient angular adjustment of the heart valve prosthesis.

Improved positioning and angular alignment for the aortic valve can be reached by the stent described in the European Patent EP 1 469 797 B1 which consists of supportive holders which can be inserted into the aortic pouches and create a defined distance to the aortic valve. Beyond this, the possibility exists to halt a failed implantation of a heart valve prosthesis and to push the valved stent ("a valve integrated into a stent") back into the catheter delivery system (more precisely the "cartridge"). Thereby, it is possible that the stent can again slide out when good positioning for the valved stent has been reached. Thus, the valved stent can be taken in and out until the optimal positioning has been achieved ("sliding technique").

A much larger problem for the optimal positioning of the new heart valve in the stent (alternatively valved stent) still exists in the following: in most cases the old, native valve will not be eliminated by the above-described technique of implantation.

This leads to the fact that the new valve which will be pressed into (partly squashed into) the old, deformed valve will be transformed into the original form. The reason for this is that the location of implantation for the valved stent is affected by the morphology, the shape and consistency of the old native valve (for instance by sclerosis or calcification of the native valve).

Therefore, the old annulus of the valve with the corresponding changed valves pouches determines to what extent and where the native valve will unfold and whether its form can develop. Hence, for the optimal function of the valve and maintenance of the atrial and ventricular function not only the anchorage/positioning is important, but also the fitting of the valve stent into the neo-annulus (old valve annulus with old valve shapes it) and with it the pushing back of the old valve.

Based on the fact that there are known problems of the valved stents, the challenge of this intervention is to produce a heart valved stent, especially a mitral valved stent, for minimally-invasive transplantation, which preferably facilitates the natural functioning of the heart.

Referring to the invention, this problem will be solved with the heart valved stent and its features from claim 1. The subclaims provide advantageous designs for setting up the intervention.

The basic idea of the invention is to produce a heart valve stent which establishes the anatomic requirements for the natural exertion of the function—like a healthy heart. In the process, the invention-related heart valve stent with its self-expanding, foldable embodiment establishes a minimally-invasive operation which assures an exact positioning and secure fixation of the valve stent. Thereby, a tension between the mitral valve and ventricle similar to the natural tension of the chordae tendineae is generated, and at the same time it will be provided that the valve parts of the old mitral valve (especially the anterior mitral valve leaflet) will not disturb the flow rate of the blood.

Therefore, it is intended that the valve stent, according to the invention, is catheter-inserted into one of the heart chambers or into the adjacent large vessels of the heart, then unfolded in one of the heart chambers, whereupon its anchoring elements are fixed in the tissue. Finally, the stent is fixed at its opposed, subvalvular wall of the heart chamber under development of a tension between the wall of the heart chamber and the proximal, supravalvular, fixed anchoring elements with anchoring sutures (hereafter referred to as neo-chordae).

The fixation of the anchoring sutures in the distal wall of the heart chamber exhibits a thrust bearing to the proximal anchoring elements which will be established by a joint or another element acting as a thrust bearing. This counter bearing can be preferentially designed also as an adjusting element for the length of the sutures.

Advantages of the heart valve stents which according to the intervention are the exact and easy fixation of the heart valve stent and improved contractility of the heart in minimally invasive operations in comparison with customary valve stents.

Preferentially, the axially, relatively to the longitudinal axis, arranged anchoring sutures are fixed according to the invention (the valve stent) with one end to the annulus of the heart valve implant, so that after development of a tension between the stent and the wall of the ventricle, the positioning and the angular arrangement of the valve can be directly impacted. The anchoring sutures can also be fixed at the distal part of the circumference of the valve stent. The connection between the anchoring sutures and the stent has to be conducted so that a tension which should run fundamentally in an axial direction relative to the long axis of the stent and is formed between the proximal anchoring elements and the distal counter bearing.

According to another preferential design of the invention, the anchoring sutures (neo-chordae) have elements to adjust the length of the anchoring sutures so that through the length of the anchoring sutures a certain tension between the heart valve stent and the heart wall can be regulated.

Thereby, an adjusting element, for example, for the individual length of sutures or for all sutures together can be allowed for. The adjusting element for the length of sutures is preferably designed small and can, for instance, be constructed in such a manner that this element shortens the suture to the desired length by rolling up the excess thread.

The construction of the elastic anchoring sutures along the axis are also preferred so that they are able to react to heart contractions without having too sutures that might negatively affect the heart function. Here the suture length should be selected so that the elasticity is not sacrificed due to the tension between the anchoring elements and the heart wall.

After adjusting the counter bearing of the adjusting element to the length of sutures, a notably beneficial design is made so that also a re-adjustment of the tension between the anchoring elements and the counter bearing, i.e. a re-tensioning of the anchoring sutures is possible without opening the heart.

Especially favored is the structure of the mitral valve stent which is fundamentally oval or u-shaped in the plane of the mitral valve annulus so that no pressure to the LVOT (left ventricular outflow tract) and/or aortic annulus is exerted. Therewith damage to the hearts function is stopped (Ma L, Tozzi P, Huber C H, Taub S, Gerelle G, von Segesser L K. Double-crowned valved stents for off-pump mitral valve replacement. Eur J Cardiothorac Surg. 2005 August; 28 (2): 194-8; discussion 198-9.). Additionally, the subvalvular apparatus also completely retains its natural anatomy and is not compromised (Boudjemline Y, Agnoletti G, Bonnet D, Behr L, Borenstein N, Sidi D, Bonhoeffer P. Steps toward the percutaneous replacement of atrioventricular valves, an experimental study. J Am Coll Cardiol. 2005 Jul. 19; 46 (2)i360-5).

This valve stent has for the natural mitral valve apparatus a completely adapted, exceedingly nestled form so that this conically tapered (cranial-caudal axis) not entirely circular (oval-like in the transversal axis) valve stent is able to attach to and abut to the natural form of the mitral valve. In the area of the anterior mitral valve annulus, the valve stent is flat and exerts almost no pressure on and does not constrict the LVOT. In the area of the posterior mitral valve annulus, it is oval and replicates a form like the posterior annulus. This valve stent forms a thin, restricted along the length (cranial-caudal) structure which in its form aligns completely to the mitral valve and thus in the area of the natural mitral valve annulus looks like a negative impression of it. In fact, the valve stent contacts the old mitral valve and the annulus, but leaves their anatomy completely unchanged.

Figure 2:
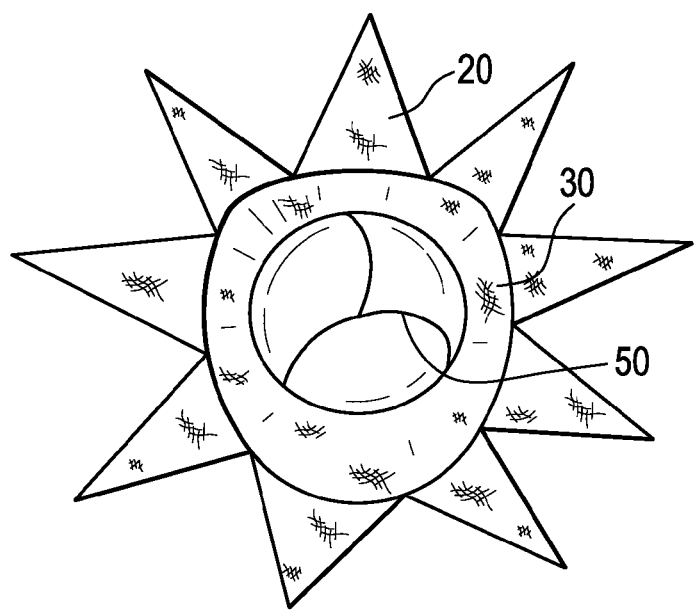
Figure 3:
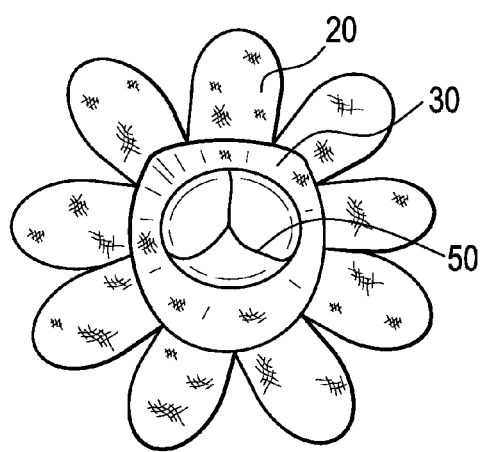
Figure 3:
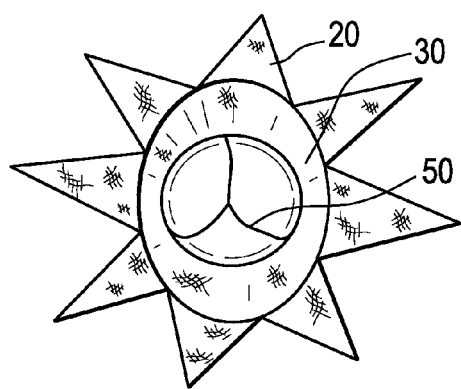
Figure 3:
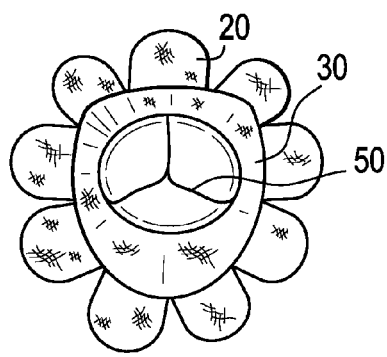
Figure 3:
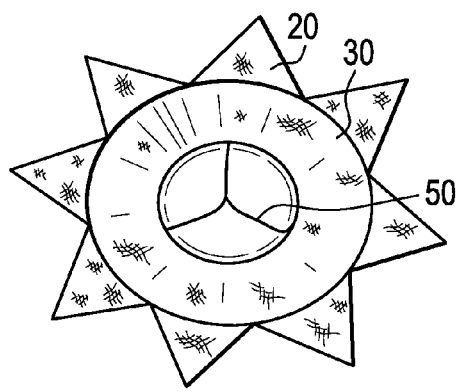
Figure 4:
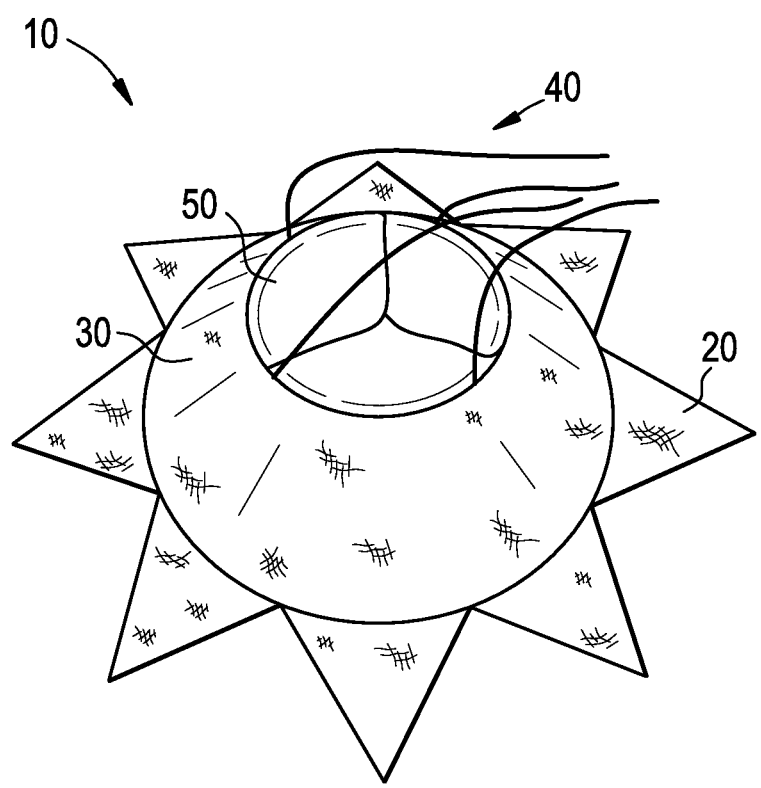
Figure 5:
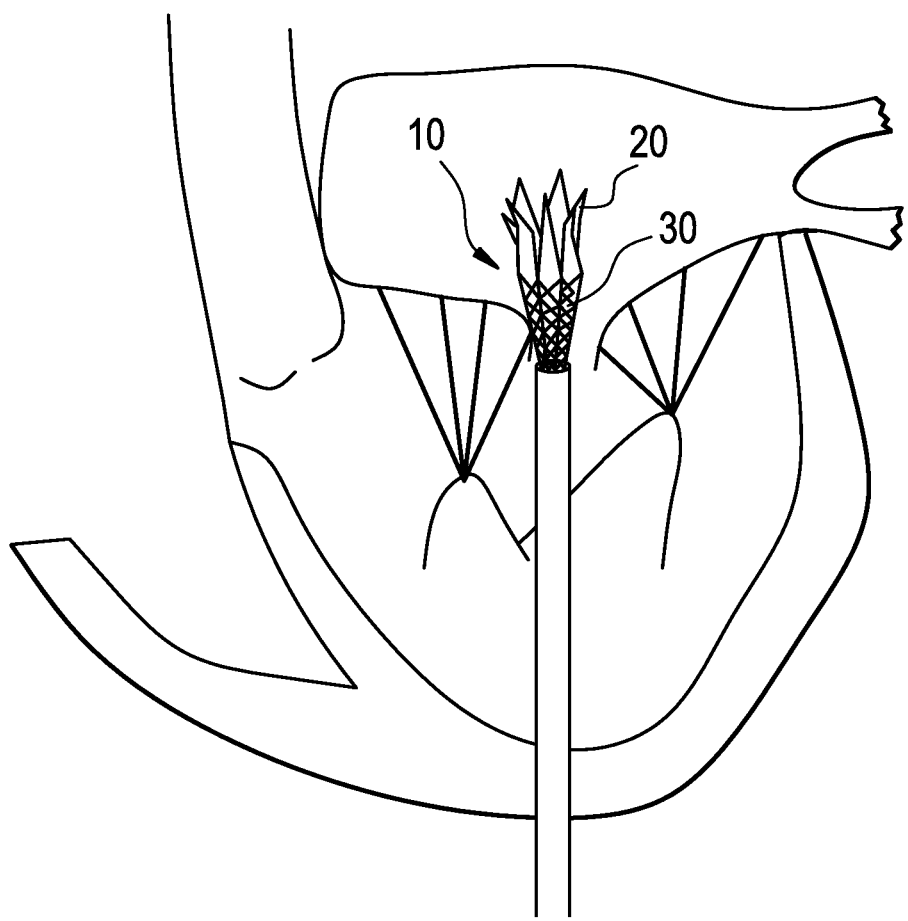
Figure 6:
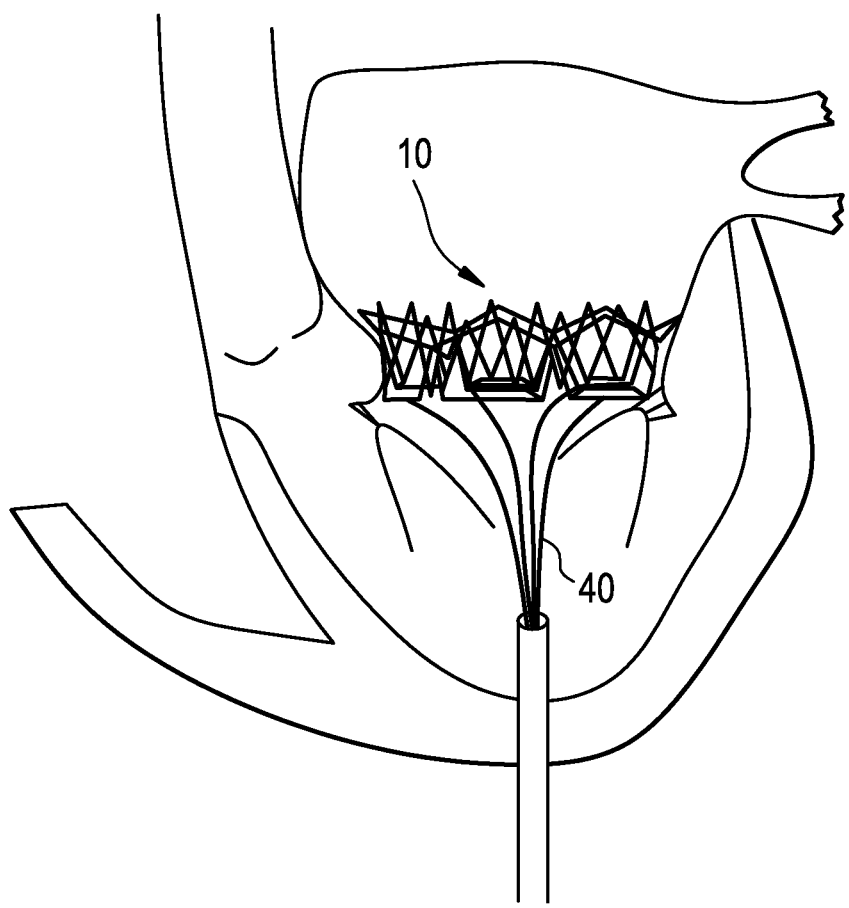
Figure 7:
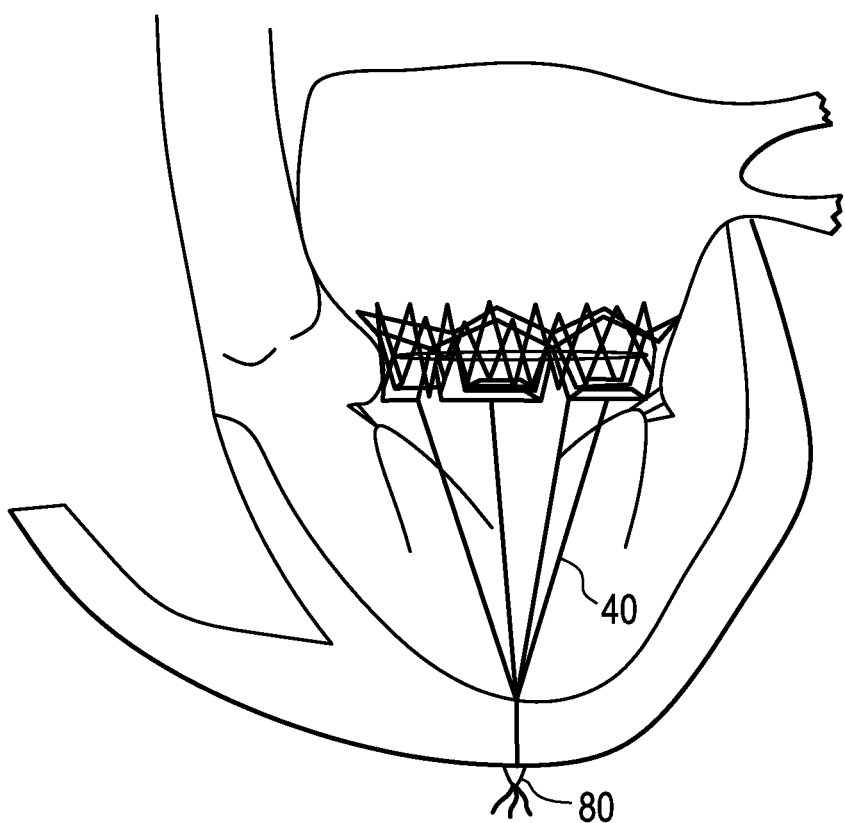
Figure 8:
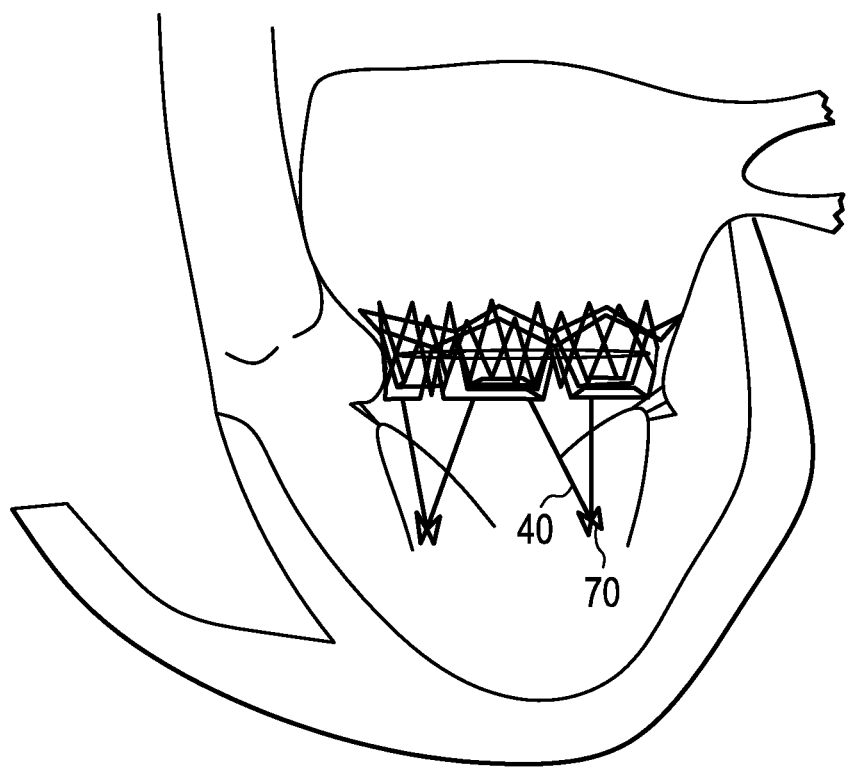
Figure 9:
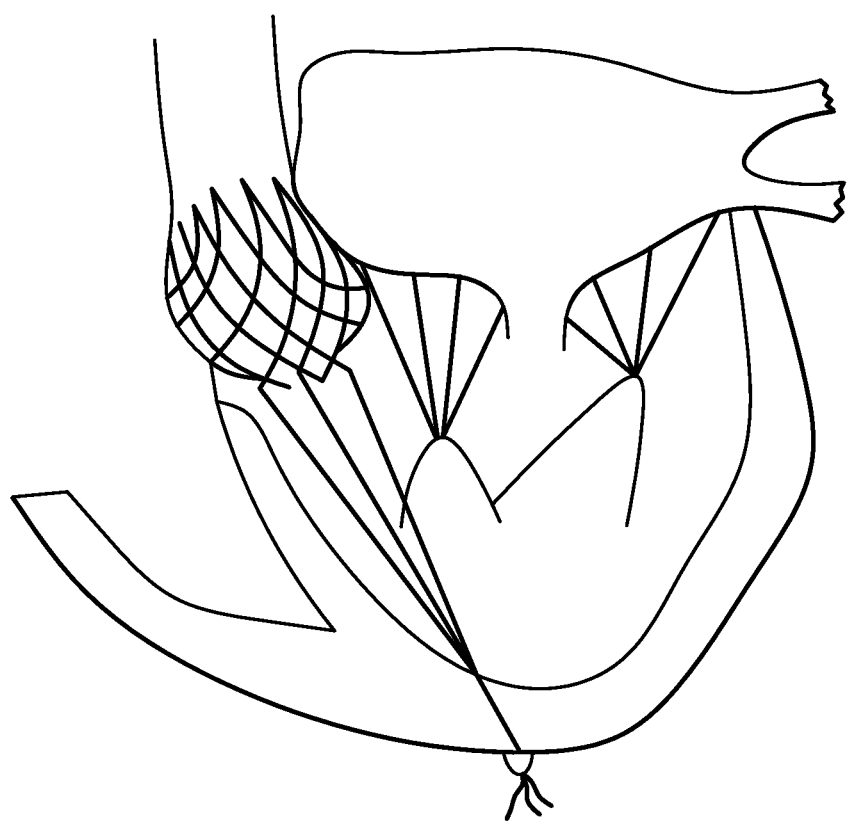
Figure 10:
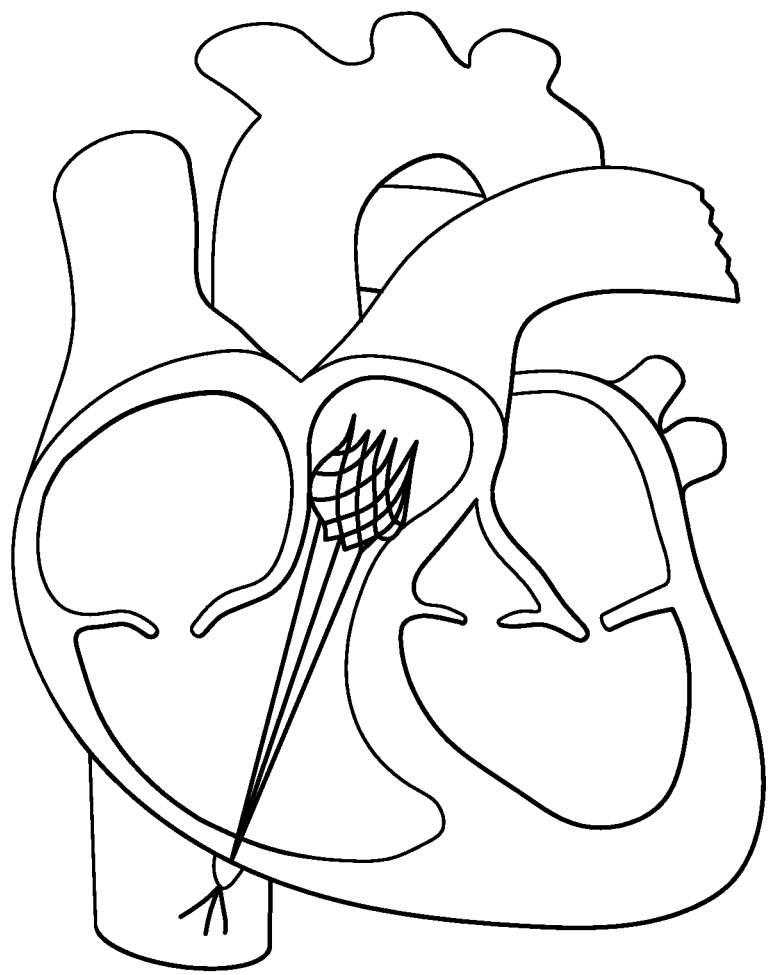
Figure 11:
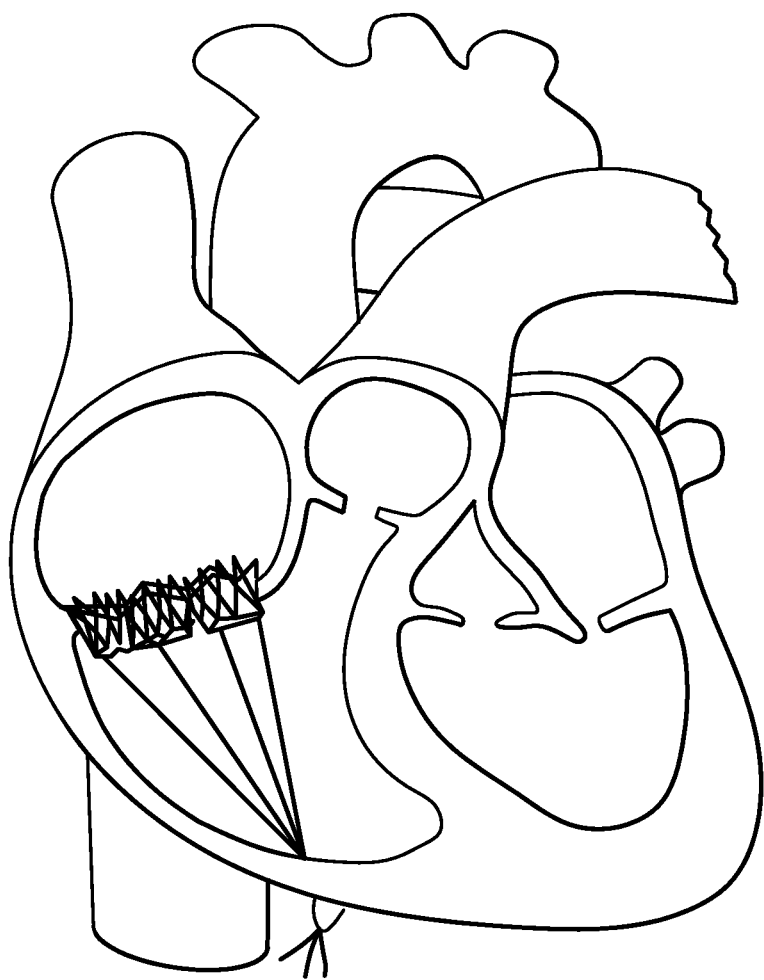
Figure 12:
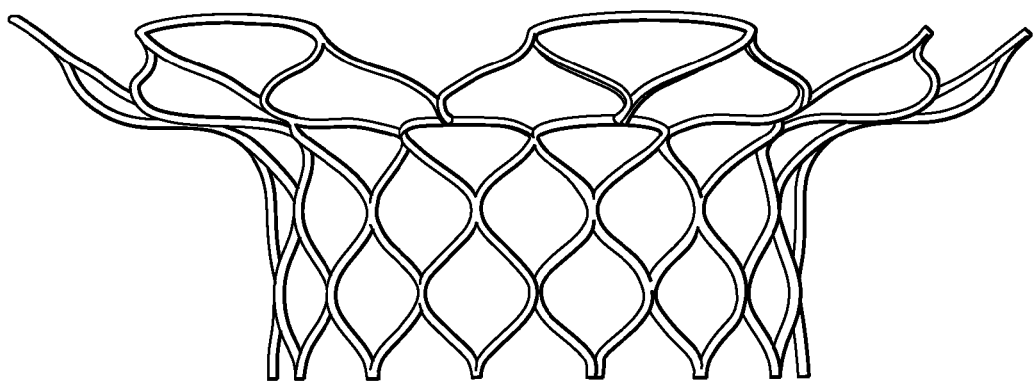
Figure 13:
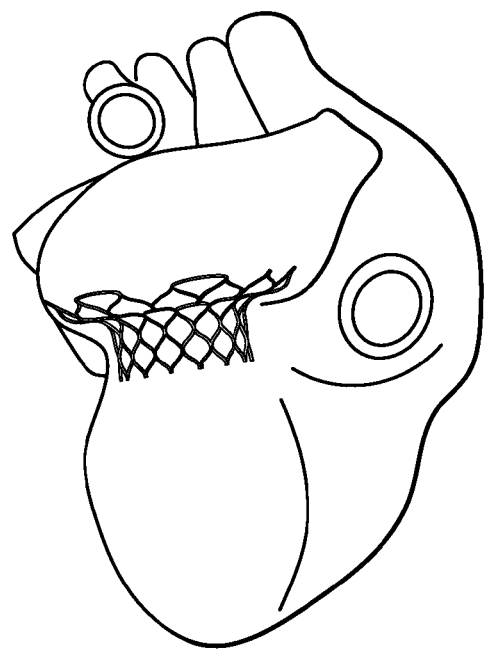

In the following the invention will be closely elucidated by means of the attached figures representing the particularly preferred execution examples. It shows:

FIG. 1 a favored execution example of the valve stent according to the invention in a schematic lateral view;

FIG. 2 the demonstrated execution example in FIG. 1 with top view from above;

FIG. 3 top view on several especially preferred valve stents according to the invention;

FIG. 4 a top view from an execution example from below;

FIG. 5 a schematic view which explains the minimally-invasive transplantation of the mitral valve stent according to the invention in a first phase of insertion of the mitral valve stent into the location of transplantation;

FIG. 6 a schematic view for the demonstration of the minimally-invasive transplantation of the mitral valve stents according to the invention in a second phase after positioning of the mitral valve;

FIG. 7 a schematic view for demonstration of the minimally invasive transplantation of the mitral valve stent after completion of the fixation of the anchoring sutures outside of the apex of the ventricular heart wall;

FIG. 8 a schematic view of an alternative, intra-cardiac fixation of the anchoring sutures in the area of papillary muscles;

FIG. 9 a schematic view of a heart valve stent which is fixed in the aortic annulus according to the invention;

FIG. 10 a schematic view of a heart valve stent which is fixed in the pulmonary position according to the invention;

FIG. 11 a schematic view of a heart valve stent which is fixed in the tricuspid position according to the invention;

FIG. 12 an especially preferred execution example of the valve stent (according to the invention) in a schematic lateral view without heart valve and anchoring sutures; and FIG. 13 a schematic dorsal, intra-cardiac view of a heart valve stent which is fixed in the mitral position according to the invention.

FIGS. 1 to 11 indicate the stent according to the invention for the implantation and fixation of heart valve prostheses in different views to show the configuration of the stents and the spatial relations of individual parts of the stent to each other in an unfolded (FIGS. 1-4 and 6-11) and in a folded condition (FIG. 5).

FIG. 1 shows a foldable mitral valve stent 10 according to the invention in a perspective lateral view. The stent 1-0 exhibits mainly three parts: proximally (supravalvularly) on stent 10 there are several serrated, arched anchoring (FIG. 3) elements circularly arranged which are able to anchor supravalvularly (respectively atrially) the valve stent 10 in an implanted condition. The preferable stent body 30 flattened to the LVOT is distally adjoined and is conical and in cross section ovally shaped (compare FIG. 2).

The stent body 30 forms a basket- or trapezoid-like figure which nestles to the mitral valve annulus and extends in the direction of the left ventricle. This stent 10 is held in the atrium due to its conically-tapered form and due to the atrial anchoring elements 20. A bi- or tri-leaflet valve 50 can be integrated into the stent body 30.

At the distal part of the stent body 30 (to the direction of the left ventricle) there are anchoring sutures 40 which are distally equipped to the stent body 30 for the anchorage of the entire stent 10. These anchoring sutures 40 provide for an anchorage in the opposed wall of the ventricle or for instance in the area of the papillary muscles 30 (proximal, medial or distal part of the papillary muscle); compare FIGS. 7 and 8. With the help of a adjusting element to regulate the length of sutures 70, these anchoring sutures 40 can be positioned and adjusted to the optimal length so that the heart valved stent 10 can be fixed and anchored.

FIG. 2 indicates the stent 10 in a top view. Thereby, it can be distinguished that stent 10 forms a neo-annulus, alternatively a stent body 30 in which the heart valve prosthesis 50 can be implanted and in which it can be fixed. Furthermore, it can be recognized that the invention-like stent 10 can be shaped asymmetrically in relation to several supravalvular (atrial) stent brackets 20.

This can be identified by the fact that the stent body 30 is oval-like and flattened on one side as seen in this figure, so it (the stent body 30) can be installed with its flattened side towards the direction of the LVOT. This flattening has the consequence that no pressure on this side towards the LVOT and towards the aortic valve can be exerted from the self-expanding stent in case the stent 10 is used, i.e. in the mitral position. Further favored embodiments of the stent 10 are indicated in FIG. 3 according to the invention.

FIG. 4 demonstrates the invention-pertaining stent 10 from a bottom view. From this it is obvious that the diameter of the atrial part to the ventricular part of the stent body 30 becomes smaller so that this looks like a truncated cone from the lateral view (compare FIG. 1). The anchoring elements 20 as well as the stent body 30 can be upholstered with cloth (i.e. synthetics, pericardium, PTFE or Goretex, etc.) to achieve better sealing between the heart valve prosthesis 50, stent body 30 and the surrounding heart structure. This sealing membrane is tapered/alternatively upholstered between the heart valve prosthesis 50, the stent body 30 or onto the atrial stent struts 20 to achieve optimal sealing of the valve between both heart chambers.

In FIGS. 5 to 7 and 8, the retrograde trans-apical implantation of the valved stent is described. The retrograde transaortic as well as the antegrade trans-atrial approach can stent above the old mitral annulus is shown in FIG. 5. A slow unfolding (preferred self-expanding) of the atrial anchoring elements 20 can be started after successful orientation with support of labeling at the valve stent 10 (not shown). The positioning in the left atrium should be done in that way that the flattened side of the stent body 5 is turned towards the direction of the LVOT (aortic valve). The stent will be further expanded.

FIG. 6 indicates the expanded valve stent 10 in the left-atrio-ventricular in-flow tract. Anchoring sutures 40 are adjusted in or outside the wall of the heart and later—as shown in FIG. 7—they will be fixed with the support of the thrust bearing 80 which is favorably designed as an adjusting element for the length of sutures. During the adjustments for the length of the anchoring sutures 40, visualization of the mitral valve apparatus (i.e. Echo, CT, NMR) is carried out so as to optimally pull the annulus of the new stent 10 toward the ventricular wall, paravalvular leakage no longer exists, the stent 10 can be fixed in a good manner, and the mitral valve annulus and—apparatus support advantageously the left ventricular function.

Alternatively to FIG. 7, the anchoring sutures 40 can also be fixed at the papillary muscles (see FIG. 8) so that these sutures 40 represent the neo chordae and take 20 over the function of the functionless chordae tendineae. The fixation of the anchoring sutures 40 at the wall of the heart in each case result from a thrust bearing 80 which can be developed as a knot or also as an independent element. It is also possible that the ventricular anchoring sutures 40 are not only affixed to the stent body 30, but also at the integrated valve itself. The caudal anchoring sutures 40 can also be fixed at any other point of the ventricle.

FIG. 7 shows the accomplished positioning and fixation of the stent 10. After the length and location of the single anchoring sutures 40 has been determined, these anchoring sutures 40 will be fixed with the suture-length adjusting elements 70, for instance, in the left ventricular wall. The suture-length adjusting element 70 is used for the optimal calibration of the length and position of the valve stent 10 and therefore for the valve prosthesis 50. Different sutures 40 can exhibit different length and fixing positions in the ventricle.

FIGS. 9 to 11 demonstrate additional examples for the application of the valve stent 10 according to the invention, whereas the stent 10 is readjusted to the particular anatomy (for the aortic- and pulmonary valve position a rather circular form (compare FIG. 3) and for the tricuspid position a rather oval form).

FIG. 12 shows an especially preferred designed execution example of the valve stent pertaining to the invention in a schematic lateral view which is shown without heart valve and anchoring sutures for a better clearness. For clarification in FIG. 12 of the positioning of the valve stent in situ, FIG. 13 demonstrates a schematic, dorsal, intra-cardiac view of a fixed heart valved stent in the mitral position according to the invention. Note the good alignment of the valved stent with the left atrial environment. Distances between the left atrial wall/mitral annulus and the valved stent are avoided. Heart valve and anchoring sutures for the ventricular apex have been omitted for simplification.

We claim:

1. A heart valve stent, comprising: a self-expanding catheter-inserted stent body section with valve leaflets disposed therein and self-expanding atrial retaining braces for atrial anchoring located at a proximal end of said stent body section said atrial retaining braces comprising a retaining skirt of a plurality of radial tooth-like projections circumferentially disposed around the proximal end of the stent body section, said tooth-like projections having a serrated, arched or triangular shape and extending radially outward from the proximal end of said stent body section at an angle bent away from the stent body section, said projections covered with a sealing membrane; and at least one ventricular anchoring suture attached to a distal end of said stent body section.

2. The heart valve stent of claim 1, further comprising wherein the ventricular anchoring suture is adjustable.

3. The heart valve stent of claim 1, further comprising wherein the heart valve implant is integrated within the lumen of the stent body section near or at the proximal end of the stent body section.

4. The heart valve stent of claim 3, wherein the heart valve implant further comprises one of the group of a circular, oval-shaped and u-shaped annulus.

5. The heart valve stent of claim 3, further comprising wherein the heart valve implant is a mitral valve.

6. The heart valve stent of claim 3, further comprising wherein the heart valve implant is a tricuspid valve.

7. The heart valve stent of claim 3, further comprising a sealing membrane between the heart valve implant and the stent.

8. The heart valve stent of claim 1, wherein the stent body is further comprised of a cross-hatching of metal wire, including but not limited to the group of diamond-shaped hatching, loop-shaped hatching, or a similar pattern.

9. The heart valve stent of claim 8, further comprising wherein the wire is made from a shape memory alloy.

10. The heart valve stent of claim 8, wherein the stent body is foldable and self-expanding.

11. A heart valve stent, shaped as a truncated cone, comprising: a foldable, self-expanding stent body section with a heart valve implant, wherein the stent body section is comprised of a cross-hatching of metal wire made from a shape memory alloy, including but not limited to the group of diamond-shaped hatching, loop-shaped hatching, or a similar pattern; self-expanding atrial retaining braces for atrial anchoring located at a proximal end of said stent body section, said atrial retaining braces comprising a retaining skirt of a plurality of radial tooth-like projections circumferentially disposed around the proximal end of the stent body section, said tooth-like projections having a serrated, arched or triangular shape and extending radially outward from the proximal end of said stent body section at an angle bent away from the stent body section, said projections covered with a sealing membrane; said heart valve implant integrated within the lumen of the stent body section at or near the proximal end of the stent body section; said heart valve stent further comprising a circular, oval-shaped or u-shaped annulus and either a mitral valve or a tricuspid valve; and, at least one ventricular anchoring suture; and wherein the ventricular anchoring suture is adjustable.

* * * * *

UNITED STATES PATENT AND TRADEMARK OFFICE
CERTIFICATE OF CORRECTION

| | | |
|---|---|---|
| PATENT NO. | : 9,095,433 B2 | Page 1 of 1 |
| APPLICATION NO. | : 13/275683 | |
| DATED | : August 4, 2015 | |
| INVENTOR(S) | : Georg Lutter | |

It is certified that error appears in the above-identified patent and that said Letters Patent is hereby corrected as shown below:

In The Claims

Claim 1, line 4 (column 6, line 67) change "section" to --section,--.

Signed and Sealed this
Twenty-sixth Day of January, 2016

Michelle K. Lee
*Director of the United States Patent and Trademark Office*